United States Patent
Mori et al.

(10) Patent No.: US 11,109,769 B2
(45) Date of Patent: Sep. 7, 2021

(54) BLOOD PRESSURE MEASURING APPARATUS AND PHYSICAL FEATURE INFORMATION CALCULATING METHOD

(71) Applicant: OMRON HEALTHCARE Co., Ltd., Kyoto (JP)

(72) Inventors: Kentaro Mori, Kyoto (JP); Shingo Yamashita, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 501 days.

(21) Appl. No.: 15/912,310

(22) Filed: Mar. 5, 2018

(65) Prior Publication Data

US 2018/0192897 A1 Jul. 12, 2018

Related U.S. Application Data

(63) Continuation of application No. PCT/JP2016/073853, filed on Aug. 15, 2016.

(30) Foreign Application Priority Data

Sep. 3, 2015 (JP) .............................. JP2015-173986

(51) Int. Cl.
*A61B 5/11* (2006.01)
*A61B 5/021* (2006.01)
(Continued)

(52) U.S. Cl.
CPC .......... *A61B 5/02116* (2013.01); *A61B 5/022* (2013.01); *A61B 5/02108* (2013.01);
(Continued)

(58) Field of Classification Search
None
See application file for complete search history.

(56) References Cited

U.S. PATENT DOCUMENTS 5,111,826 A * 5/1992 Nasiff .................... A61B 5/025
                                                                600/485
5,724,265 A * 3/1998 Hutchings ............ A43B 3/0005
                                                                235/105
(Continued)

FOREIGN PATENT DOCUMENTS

CN        103099611 A      5/2013
CN        104602593 A      5/2015
(Continued)

OTHER PUBLICATIONS

Office Action issued in corresponding Chinese Application No. 201680051306.7, dated Feb. 6, 2020 (5 pages).
(Continued)

*Primary Examiner* — Jason M Sims
*Assistant Examiner* — James Stewart Stambaugh, III
(74) *Attorney, Agent, or Firm* — Osha Bergman Watanabe & Burton LLP

(57) ABSTRACT

A blood pressure measuring apparatus includes: a triaxial acceleration sensor; an information output section which outputs information for guiding an arm of the person on which the blood pressure measuring apparatus is worn, to a pair of a first posture and a second posture between which a position of the wrist is different; a posture determiner which determines that the arm has been in each of the pair of the postures, based on an output signal of the triaxial acceleration sensor after the output of the information; and a physical feature information calculator which calculates physical feature information of the person based on moving acceleration information detected by the triaxial acceleration sensor in a period between when the arm is in one of the pair of the postures and when the arm is in the other of the pair of the postures.

12 Claims, 7 Drawing Sheets

(51) Int. Cl.
  *A61B 5/022* (2006.01)
  *A61B 5/00* (2006.01)
  *A61B 5/107* (2006.01)

(52) U.S. Cl.
  CPC ............ *A61B 5/1116* (2013.01); *A61B 5/681* (2013.01); *A61B 5/1071* (2013.01); *A61B 5/1072* (2013.01); *A61B 5/11* (2013.01); *A61B 5/6824* (2013.01); *A61B 2560/0247* (2013.01); *A61B 2562/0219* (2013.01)

(56) References Cited

U.S. PATENT DOCUMENTS

| | | | |
|---|---|---|---|
| 2004/0077958 A1 | 4/2004 | Kato et al. | |
| 2007/0055163 A1* | 3/2007 | Asada | A61B 5/02225 600/485 |
| 2009/0012409 A1* | 1/2009 | Roenneberg | A61B 5/681 600/485 |
| 2010/0274143 A1* | 10/2010 | Kim | A61B 5/022 600/493 |
| 2010/0298650 A1* | 11/2010 | Moon | A61B 5/044 600/301 |
| 2011/0025817 A1* | 2/2011 | Carter | H04N 7/141 348/14.02 |
| 2011/0118613 A1 | 5/2011 | Yokoyama et al. | |
| 2012/0270654 A1* | 10/2012 | Padovani | G06F 3/017 463/36 |
| 2013/0165800 A1* | 6/2013 | Shimizu | A61B 5/0507 600/485 |
| 2013/0211774 A1* | 8/2013 | Bentley | A61B 5/6895 702/145 |
| 2013/0237865 A1 | 9/2013 | Sato et al. | |
| 2015/0182147 A1 | 7/2015 | Sato et al. | |
| 2016/0081572 A1* | 3/2016 | Hong | A61B 5/02055 600/301 |

FOREIGN PATENT DOCUMENTS

| | | |
|---|---|---|
| JP | 2011-104073 A | 6/2011 |
| JP | 2014-068825 A | 4/2014 |
| WO | 02/39893 A1 | 5/2002 |

OTHER PUBLICATIONS

International Search Report issued in Application No. PCT/JP2016/073853, dated Oct. 11, 2016 (1 page).
Written Opinion issued in Application No. PCT/JP2016/073853, dated Oct. 11, 2016 (4 pages).

* cited by examiner

BLOOD PRESSURE MEASURING APPARATUS AND PHYSICAL FEATURE INFORMATION CALCULATING METHOD

CROSS-REFERENCE TO RELATED APPLICATION(S)

This application is a continuation of PCT application No. PCT/JP2016/073853, which was filed on Aug. 15, 2016 based on Japanese Patent Application (No. 2015-173986) filed on Sep. 3, 2015, the contents of which are incorporated herein by reference.

BACKGROUND

1. Technical Field

The present invention relates to a blood pressure measuring apparatus and a physical feature information calculating method.

2. Background Art

Generally, a blood pressure measuring apparatus can obtain an accurate blood pressure value when a measurer of the blood pressure measuring apparatus is placed at the height of a heart to make measurement. However, a wrist on which the measurer of the wrist blood pressure measuring apparatus is worn is a part which can move freely. For this reason, it is difficult to accurately adjust the wrist to the same height as the height of the heart. Therefore, there is a case that the blood pressure value cannot be measured accurately.

In order to solve the aforementioned problem, WO2002/039893 discloses a blood pressure measuring apparatus which detects a difference in height between a heart and a wrist based on body part feature information of a person to be measured such as a forearm length and an upper arm length inputted by the person to be measured manually, and information indicating a state of the arm of the person to be measured such as an angle of the forearm or an angle of the upper arm detected by an acceleration sensor etc., and performs a process of correcting a blood pressure value in accordance with the detected difference.

In the method described in WO2002/039893, it is necessary to obtain physical feature information of the person to be measured in advance and the physical feature information is expected to be inputted manually. In order to input the physical feature information, it is necessary to measure the forearm length or the upper arm length by a tape measure etc. beforehand.

When a measurement error is generated due to the measurement, calculation accuracy of the difference in height between the part where the blood pressure value is measured and the heart is lowered. In addition, since it is necessary to use the tape measure to make measurement, the measurement work is a burden to the person to be measured.

It has been known that the forearm length or the upper arm length is correlated to a stature. Therefore, the stature of the person to be measured may be manually inputted so that the forearm length or the upper arm length can be calculated from the inputted stature. However, also in this case, it is not possible to eliminate a possibility that an error may be generated in the calculated forearm length or upper arm length and an actual forearm length or upper arm length of the person to be measured.

In addition, when there is a simple input mistake during manual input of the physical feature information or the stature, the blood pressure value cannot be measured accurately.

SUMMARY

The invention has been accomplished in consideration of the aforementioned circumstances. An object of the invention is to provide a blood pressure measuring apparatus and a physical feature information calculating method, in which physical feature information of a person to be measured necessary for calculating a difference in height between a measured part and a heart can be obtained accurately by simple work.

According to an aspect of the invention, there is provided a blood pressure measuring apparatus which is adapted to be worn on a wrist of a person to be measured to measure a blood pressure value of the person to be measured, the blood pressure measuring apparatus comprising: a triaxial acceleration sensor; an information output section which is configured to output information for guiding an arm of the person to be measured on which the blood pressure measuring apparatus is worn, to a pair of a first posture and a second posture between which a position of the wrist is different; a posture determiner which is configured to determine that the arm has been in each of the pair of the postures, based on an output signal of the triaxial acceleration sensor after the output of the information; and a physical feature information calculator which is configured to calculate physical feature information of the person to be measured based on moving acceleration information detected by the triaxial acceleration sensor in a period between when the arm is in one of the pair of the postures and when the arm is in the other of the pair of the postures.

According to an aspect of the invention, there is also provided a physical feature information calculating method for calculating physical feature information of a person, the physical feature information calculating method comprising: outputting information for guiding an arm of the person to a pair of a first posture and a second posture between which a position of a wrist of the person is different; determining that the arm has been in each of the pair of the postures based on an output signal of a triaxial acceleration sensor after the output of the information, the triaxial acceleration sensor adapted to be worn on the wrist of the person; and calculating the physical feature information of the person based on moving acceleration information detected by the triaxial acceleration sensor in a period between when the arm is in one of the pair of the postures and when the arm is in the other of the pair of the postures.

DESCRIPTION OF EXEMPLARY EMBODIMENTS

An embodiment of the invention will be described below with reference to the drawings.

Figure 1:
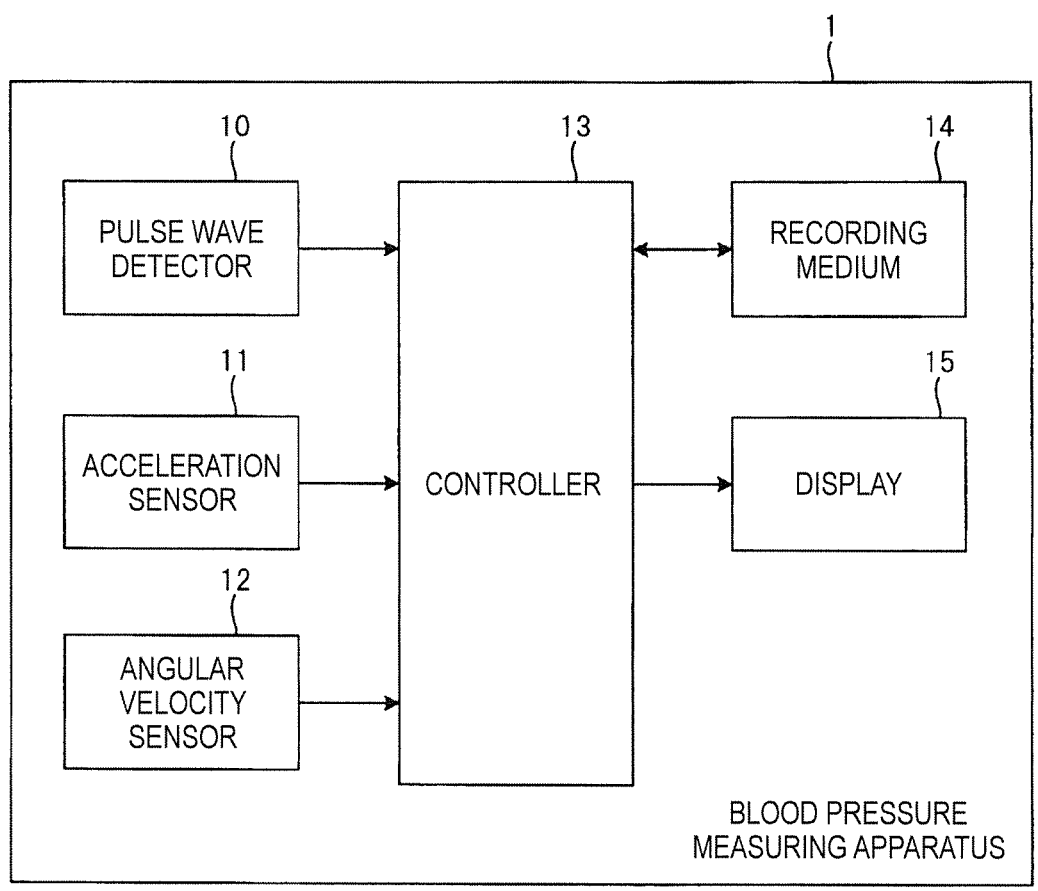
FIG. 1 is a block diagram showing the configuration of a blood pressure measuring apparatus 1 which is an embodiment of the invention.

FIG. 1 is a block diagram showing the configuration of a blood pressure measuring apparatus 1 which is an embodiment of the invention. The blood pressure measuring apparatus 1 is a portable type which is used to be worn on a wrist of a person to be measured regarded as a living body.

The blood pressure measuring apparatus 1 includes a pulse wave detector 10, an acceleration sensor 11, an angular velocity sensor 12, a controller 13 which generally controls the blood pressure measuring apparatus 1 as a whole, a recording medium such as a flash memory, an ROM (Read Only Memory) or a memory card, and a display 15 which is constituted by a liquid crystal display etc.

The pulse wave detector 10 detects a pulse wave in a noninvasive manner from a wrist of a person to be measured. The pulse wave detector 10 is used for detecting a pressure pulse wave as the pulse wave, for example, by a tonometry method. The pulse wave detector 10 may detect a volume pulse wave as the pulse wave. The pulse wave detector 10 may detect a pulse wave by reflected light obtained from an artery irradiated with light.

The acceleration sensor 11 detects a move of the wrist of the person to be measured as acceleration information. In the embodiment, a triaxial acceleration sensor for detecting triaxial acceleration in X-, Y- and Z-axis directions is used as the acceleration sensor 11.

The acceleration sensor 11 is mounted in the apparatus so that the Z-axis direction is parallel with an extension direction of an arm (a direction connecting an elbow and the wrist to each other) when the blood pressure measuring apparatus 1 is worn on the wrist.

The angular velocity sensor 12 detects a posture (a roll angle and a pitch angle) of the wrist of the person to be measured as angular velocity information.

Figure 2:
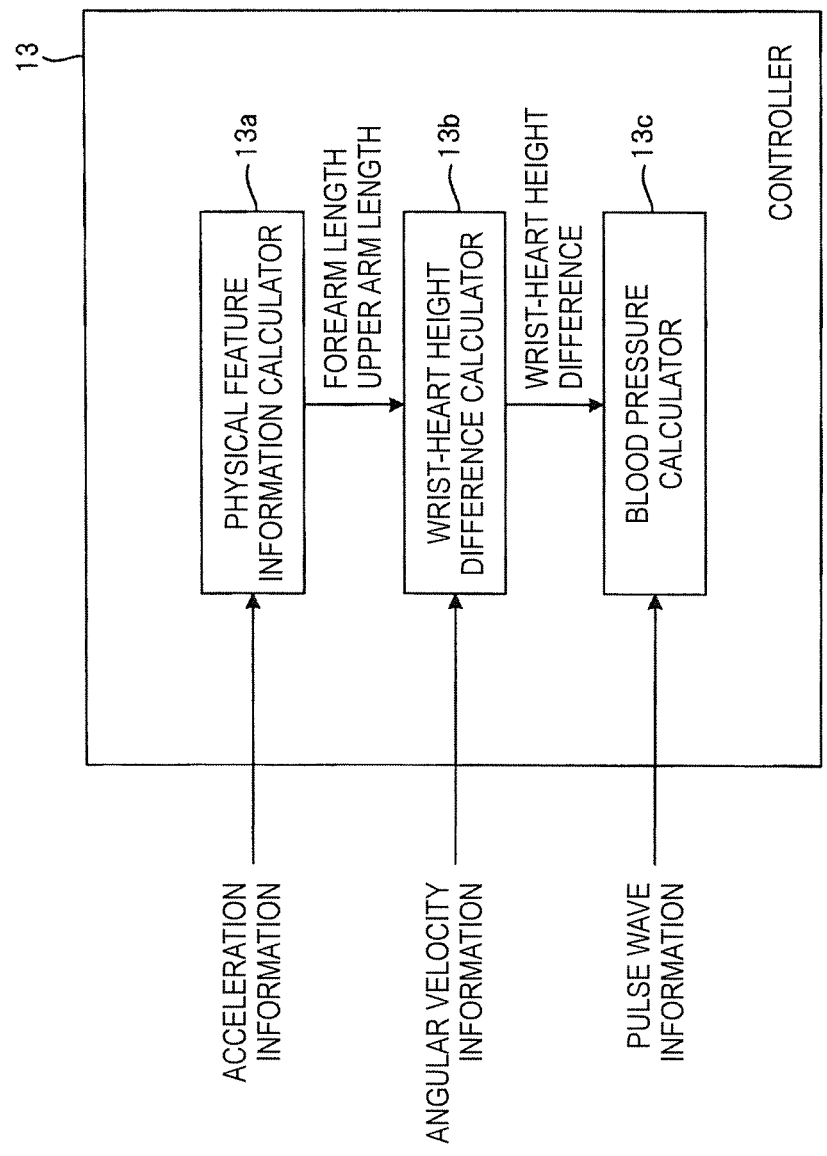
FIG. 2 is a functional block diagram of a controller 13 in FIG. 1.

FIG. 2 is a functional block diagram of the controller 13 in FIG. 1.

The controller 13 is mainly constituted by a processor and a memory such as an RAM (Random Access Memory) or an ROM. When the processor executes a program stored in the ROM, the controller 13 functions as a physical feature information calculator 13a, a wrist-heart height difference calculator 13b, and a blood pressure calculator 13c.

The physical feature information calculator 13a calculates a forearm length (first distance) and an upper arm length (third distance) of the person to be measured based on the acceleration information detected by the acceleration sensor 11. The forearm length means a distance between the elbow and the wrist of the person to be measured. The upper arm length means a distance between a shoulder and the elbow of the person to be measured.

The wrist-heart height difference calculator 13b calculates a difference in height between the wrist and the heart of the person to be measured by a known method exemplified in WO2002/039893 based on the forearm length and the upper arm length of the person to be measured calculated by the physical feature information calculator 13a and an angle of the wrist based on the angular velocity information detected by the angular velocity sensor 12.

The blood pressure calculator 13c calculates a blood pressure value per beat based on the pulse wave detected by the pulse wave detector 10. The blood pressure value includes systolic blood pressure SBP, diastolic blood pressure DBP, and mean blood pressure MBP etc.

The blood pressure calculator 13c corrects the blood pressure value calculated based on the pulse wave, in accordance with the difference in height between the wrist and the heart calculated by the wrist-heart height difference calculator 13b, and records the corrected blood pressure value as a final blood pressure value into the recording medium 14.

Next, a forearm length calculating process and an upper arm length calculating process to be performed by the physical feature information calculator 13a will be described specifically.

Figure 3:
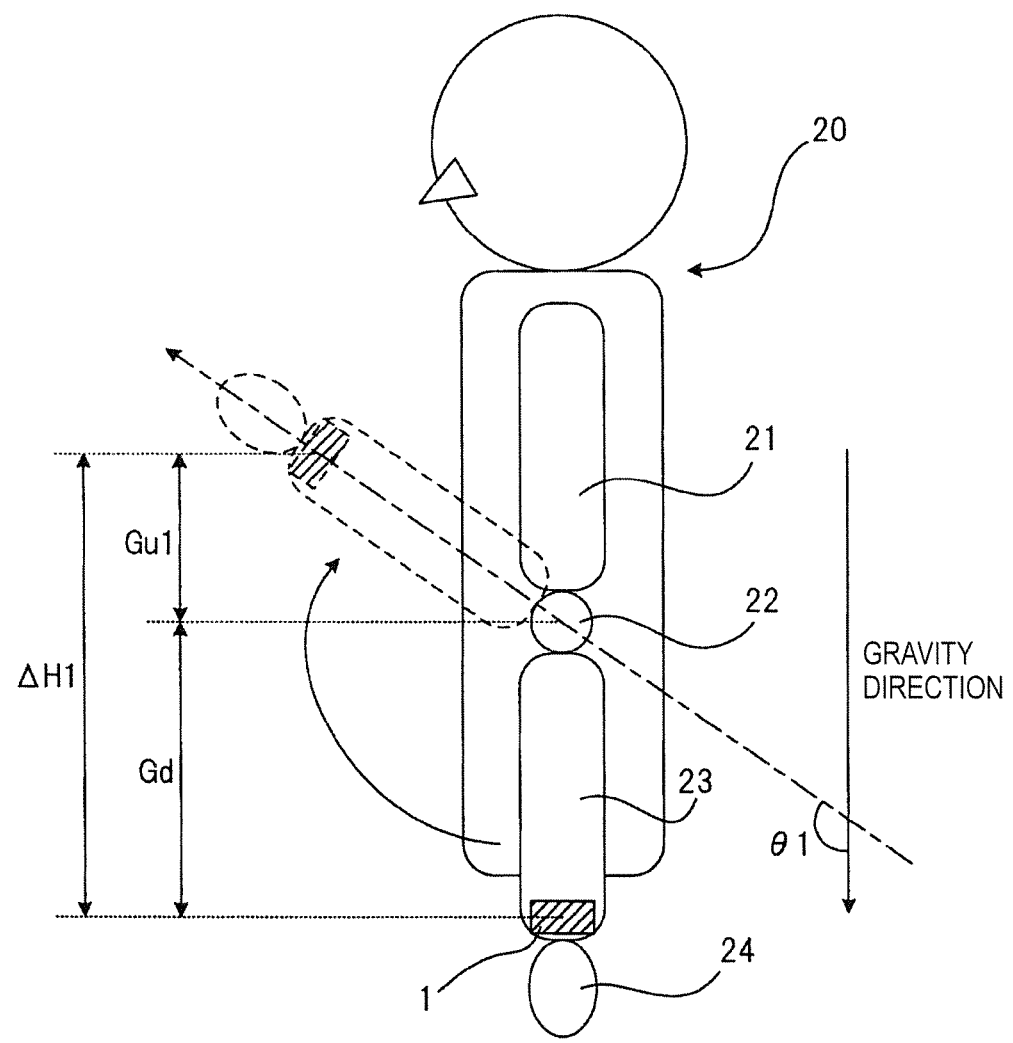
FIG. 3 is a view for explaining a forearm length calculating process to be performed by a physical feature information calculator 13a in FIG. 2.

FIG. 3 is a view for explaining the forearm length calculating process to be performed by the physical feature information calculator 13a in FIG. 2.

A person to be measured 20 is illustrated in FIG. 3. The reference numeral 21 designates an upper arm of a left arm of the person to be measured; the reference numeral 22 designates an elbow of the left arm of the person to be measured; the reference numeral 23 designates a forearm of the left arm of the person to be measured; and the reference numeral 24 designates a left hand of the person to be measured. The blood pressure measuring apparatus 1 in FIG. 1 is worn on a left wrist of the person to be measured.

Assume that a predetermined first move is performed by the person to be measured in order to calculate a forearm length of the person to be measured by the blood pressure measuring apparatus 1. The first move is a move in which the person to be measured whose arm has been already put down raises the wrist to a higher position than the elbow 22 with the elbow 22 as a rotation center without changing the position of the elbow 22.

By the first move, the arm of the person to be measured 20 shifts from a first posture to a second posture. In the first posture, a shoulder, the elbow and the wrist of the person to be measured 20 are arranged in a gravity direction. In the second posture, the shoulder and the elbow 22 of the person to be measured 20 are arranged in the gravity direction and an angle θ1 between a direction connecting the elbow 22 and the wrist of the person to be measured to each other (a direction indicated by an arrow of an alternate long and short dash line in FIG. 3) and the gravity direction is larger than 90°. Incidentally, the first move may be a move for changing the posture from the second posture to the first posture.

In FIG. 3, the forearm 23 and the hand 24 are designated by a broken line when the arm of the person to be measured is in the state of the second posture.

In FIG. 3, Z-axis direction acceleration information detected by the acceleration sensor 11 in the state of the first posture is regarded as first acceleration information Gd. Z-axis direction acceleration information detected by the acceleration sensor 11 in the state of the second posture is regarded as second acceleration information Gu1.

The physical feature information calculator 13a performs second-order integration in which triaxial acceleration information of a world coordinate system detected by the acceleration sensor 11 in a period in which the first move is performed (in a process of movement from the state of the first posture to the state of the second posture) is integrated twice with respect to a time corresponding to a length of the period. Thus, the physical feature information calculator 13a calculates first displacement information ΔH1 [cm], which is a displacement amount of a height of the wrist of the person to be measured 20 in the period.

The physical feature information calculator 13a calculates the forearm length of the person to be measured 20 based on the first displacement information ΔH1 [cm], the first acceleration information Gd, and the second acceleration information Gu1.

More specifically, the physical feature information calculator 13a calculates the forearm length of the person to be measured 20 by arithmetic processing of the following expression (1) based on the first displacement information ΔH1 [cm], and a first ratio of an absolute value of the first acceleration information Gd to the sum of the absolute value of the first acceleration information Gd and an absolute value of the second acceleration information Gu1.

$$\text{Forearm Length} = \Delta H1 \times \{|Gd|/(|Gd|+|Gu1|)\} \quad (1)$$

The forearm length corresponds to a displacement amount of the wrist in the gravity direction until the angle θ1 becomes 90° (the positions of the elbow 22 and the wrist in the gravity direction agree with each other) after the wrist is raised from the first posture.

That is, a value, which is obtained by second-order integrating the triaxial acceleration information of the world coordinate system detected by the acceleration sensor 11 until the angle θ1 is changed to 90° from the first posture with respect to the time required until the angle θ1 is changed to 90° from the first posture, corresponds to the forearm length.

In this manner, the person to be measured is requested to perform the move to raise the arm from the first posture until the angle θ1 becomes 90° accurately. When the triaxial acceleration information outputted from the acceleration sensor 11 during the period of the move is second-order integrated with respect to the time, the forearm length can be obtained.

However, when the person to be measured is requested to perform such a move to change the angle θ1 to 90°, this request imposes a burden on the person to be measured. In addition, since it is actually difficult to adjust the angle θ1 to 90° accurately, there is a possibility that an error may be generated in the forearm length.

On the other hand, the aforementioned first move in which the person to be measured may stop the arm at any time point when the angle θ1 is an arbitrary value larger than 90° imposes no burden on the person to be measured. Based on such a reason, the person to be measured is requested to perform the first move to change the posture from the first posture to the second posture in the embodiment.

The first displacement information ΔH1 obtained when the first move is performed includes a first displacement component in a period in which the angle θ1 is changed from 0° to 90°, and a second displacement component in a period in which the angle θ1 is larger than 90°.

A ratio between the first displacement component and the second displacement component is equal to a ratio between the absolute value of the first acceleration information Gd and the absolute value of the second acceleration information Gu1. Accordingly, the forearm length can be calculated in accordance with the aforementioned expression (1).

Figure 4:
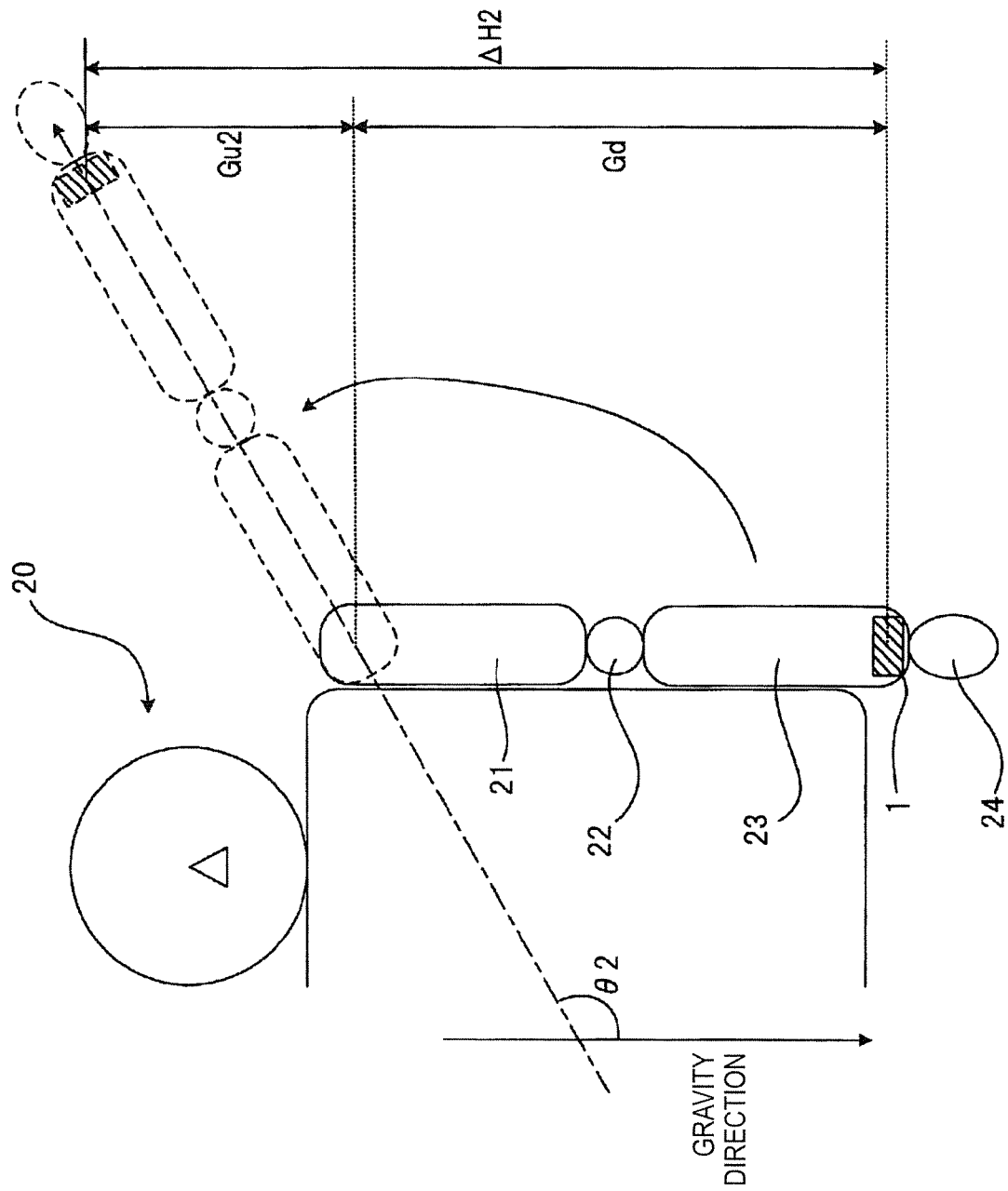
FIG. 4 is a view for explaining an upper arm length calculating process to be performed by the physical feature information calculator 13a in FIG. 2.

FIG. 4 is a view for explaining the upper arm length calculating process to be performed by the physical feature information calculator 13a in FIG. 2. FIG. 4 is a front view of the person to be measured 20. In a similar manner to or the same manner as FIG. 3, the left upper arm 21, the left elbow 22, the left forearm 23 and the left hand 24 of the person to be measured 20 are illustrated in FIG. 4.

Assume that a predetermined second move is performed by the person to be measured in order to calculate an upper arm length of the person to be measured by the blood pressure measuring apparatus 1. The second move is a move in which the person to be measured whose arm has already been put down raises the wrist to a higher position than the shoulder with the shoulder as a rotation center while keeping the arm straight.

By the second move, the arm of the person to be measured 20 shifts from the first posture to a third posture. In the first posture, the shoulder, the elbow and the wrist of the person to be measured 20 are arranged in the gravity direction. In the third posture, an angle θ2 between a direction connecting the shoulder, the elbow 22 and the wrist of the person to be measured 20 to one another (a direction indicated by an arrow of an alternate long and short dash line in FIG. 4) and the gravity direction is larger than 90°. Incidentally, the second move may be a move for changing the posture from the third posture to the first posture.

In FIG. 4, the upper arm 21, the elbow 22, the forearm 23 and the hand 24 are designated by a broken line when the arm of the person to be measured is in the state of the third posture.

In FIG. 4, Z-axis direction acceleration information detected by the acceleration sensor 11 in the state of the first posture is regarded as first acceleration information Gd, in the same manner as in FIG. 3. Z-axis direction acceleration information detected by the acceleration sensor 11 in the state of the third posture is regarded as third acceleration information Gu2.

The physical feature information calculator 13a performs second-order integration in which triaxial acceleration information of a world coordinate system detected by the acceleration sensor 11 in a period in which the second move is performed (in a process of movement from the state of the first posture to the state of the third posture) is integrated twice with respect to a time corresponding to a length of the period. Thus, the physical feature information calculator 13a calculates second displacement information ΔH2 [cm], which is a displacement amount of a height of the wrist of the person to be measured 20 in the period.

The physical feature information calculator 13a calculates an upper limb length (a distance between the shoulder and the wrist; a second distance) of the person to be measured 20 based on the second displacement information ΔH2 [cm], the first acceleration information Gd, and the third acceleration information Gu2.

More specifically, the physical feature information calculator 13a calculates the upper limb length of the person to be measured 20 by arithmetic processing of the following expression (2) based on the second displacement information ΔH2 [cm], and a second ratio of an absolute value of the first acceleration information Gd to the sum of the absolute value of the first acceleration information Gd and an absolute value of the third acceleration information Gu2.

$$\text{Upper Limb Length} = \Delta H2 \times \{|Gd|/(|Gd|+|Gu2|)\} \quad (2)$$

The upper limb length corresponds to a displacement amount of the wrist in the gravity direction until the angle θ2 becomes 90° (the positions of the shoulder and the wrist in the gravity direction agree with each other) after the arm is raised from the first posture.

That is, a value, which is obtained by second-order integrating the triaxial acceleration information of the world coordinate system detected by the acceleration sensor 11 until the angle θ2 is changed to 90° from the first posture with respect to the time required until the angle θ2 is changed to 90° from the first posture, corresponds to the upper limb length.

In this manner, the person to be measured is requested to perform the move to raise the arm from the first posture until the angle θ2 becomes 90° accurately. When the triaxial acceleration information outputted from the acceleration sensor 11 during the period of the move is second-order integrated with respect to the time, the upper limb length can be obtained.

However, when the person to be measured is requested to perform such a move to change the angle θ2 to 90°, this request imposes a burden on the person to be measured. In addition, since it is actually difficult to adjust the angle θ2 to 90° accurately, there is a possibility that an error may be generated in the upper limb length.

On the other hand, the aforementioned second move in which the person to be measured may stop the arm at any time point when the angle θ2 is an arbitrary value larger than 90° imposes no burden on the person to be measured. Based on such a reason, the person to be measured is requested to perform the second move to change the posture from the first posture to the third posture in the embodiment.

The second displacement information ΔH2 obtained when the second move is performed includes a third displacement component in a period in which the angle θ2 is changed from 0° to 90°, and a fourth displacement component in a period in which the angle θ2 is larger than 90°.

A ratio between the third displacement component and the fourth displacement component is equal to a ratio between the absolute value of the first acceleration information Gd and the absolute value of the third acceleration information Gu2. Accordingly, the upper limb length can be calculated in accordance with the aforementioned expression (2).

The physical feature information calculator 13a calculates the upper arm length by subtracting the forearm length from the upper limb length calculated in the aforementioned manner.

Figure 5:
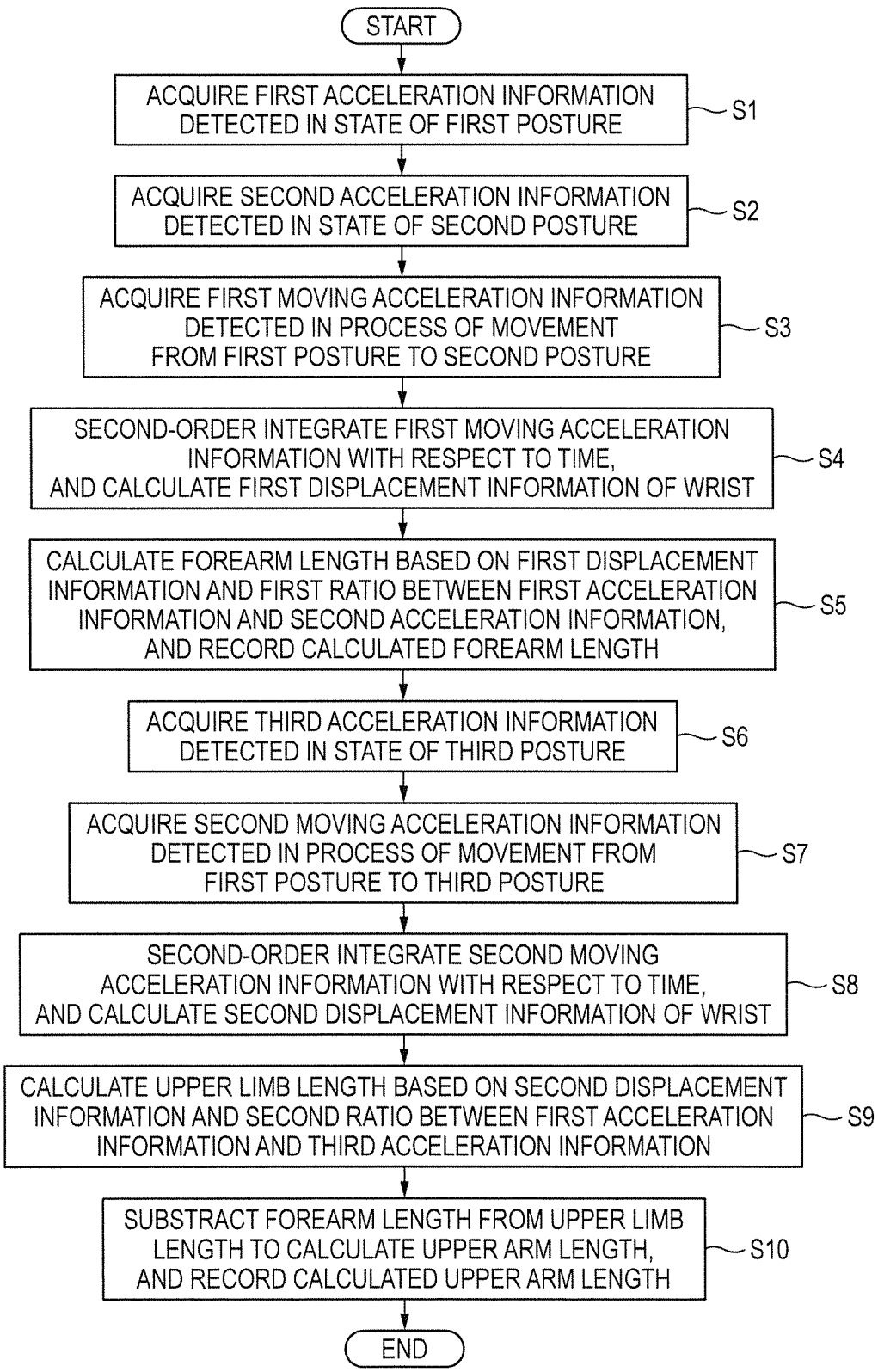
FIG. 5 is a flow chart for explaining moves of the blood pressure measuring apparatus 1 in FIG. 1.

FIG. 5 is a flow chart for explaining a calculating process of the forearm length and the upper arm length to be performed by the physical feature information calculator 13a in FIG. 2.

A mode for calculating the forearm length and the upper arm length is provided in the blood pressure measuring apparatus 1. When the mode is set, the controller 13 uses, for example, the display 15 to issue an instruction to the person to be measured to assume the first posture and change the posture from this state to the second posture, and then to issue an instruction to the person to be measured to assume the first posture again and change the posture from this state to the third posture. The pieces of information about the instructions displayed on the display 15 are pieces of information for guiding the arm of the person to be measured to the first posture and the second posture and to the first posture and the third posture respectively. The controller 13 serves as an information output section.

As an instruction method, for example, a character imitating the person to be measured is displayed on the display 15, and the character is moved to plainly demonstrate a move from the first posture to the second posture and a move from the first posture to the third posture.

Alternatively, the controller 13 may output a message "please put your arm straight down" from a not-shown speaker to request the person to be measured to assume the first posture. Next, the controller 13 may output a message "in this state, please raise your wrist higher than your elbow and stop it while keeping the position of your elbow fixed" from the speaker to request the person to be measured to assume the second posture.

In a similar manner or the same manner, the controller 13 may output a message "please put your arm straight down" from the speaker to request the person to be measured to assume the first posture. Next, the controller 13 may output a message "in this state, please raise your wrist higher than your shoulder and stop it while leaving your arm stretched out" from the speaker to request the person to be measured to assume the third posture. The pieces of information outputted from the speaker are pieces of information for guiding the arm of the person to be measured to the first posture and the second posture and to the first posture and the third posture respectively.

Alternatively, configuration may be made in advance so that the blood pressure measuring apparatus 1 can communicate with an electronic device with a display owned by the person to be measured, such as a smartphone. The controller 13 transmits, to the electronic device, the pieces of information for guiding the arm of the person to be measured to the first posture and the second posture and to the first posture and the third posture respectively. The electronic device may display the pieces of information received from the blood pressure measuring apparatus 1 on the display, so that the posture guidance can be given to the person to be measured.

The controller 13 determines whether the person to be measured has assumed the first posture or not, based on Z-axis acceleration information. The controller 13 determines a state in which the sign of the Z-axis acceleration information detected by the acceleration sensor 11 is negative and a variation of the Z-axis direction acceleration information is not larger than a threshold for a predetermined time, as the first posture.

In addition, the controller 13 determines a state in which the sign of the Z-axis acceleration information detected by the acceleration sensor 11 is positive and a variation of the Z-axis direction acceleration information is not larger than a threshold for a predetermined time, as the second posture or the third posture. The controller 13 functions as a posture determiner.

When the move from the first posture to the second posture and the move from the first posture to the third posture are performed by the person to be measured, the physical feature information calculator 13a of the controller 13 acquires first acceleration information (Z-axis acceleration information) detected by the acceleration sensor 11 in the state of the first posture (step S1).

Next, the physical feature information calculator 13a acquires second acceleration information (Z-axis acceleration information) detected by the acceleration sensor 11 in the state of the second posture (step S2).

Next, the physical feature information calculator 13a acquires first moving acceleration information (triaxial acceleration information) detected by the acceleration sensor 11 in a process of movement from the first posture to the second posture (step S3).

Next, the physical feature information calculator 13a second-order integrates the triaxial acceleration information acquired in the step S3 with respect to a time required until the posture is changed from the first posture to the second posture, and calculates a displacement amount (first displacement information ΔH1) of the wrist of the person to be measured in the process of movement from the first posture to the second posture (step S4).

Next, the physical feature information calculator 13a calculates a forearm length of the person to be measured by arithmetic processing of the expression (1) based on the first displacement information ΔH1 and a first ratio between the first acceleration information acquired in the step S1 and the second acceleration information acquired in the step S2, and records the calculated forearm length into the recording medium 14 (step S5).

Next, the physical feature information calculator 13a acquires third acceleration information (Z-axis acceleration information) detected by the acceleration sensor 11 in the state of the third posture (step S6).

Next, the physical feature information calculator 13a acquires second moving acceleration information (triaxial acceleration information) detected by the acceleration sensor 11 in a process of movement from the first posture to the third posture (step S7).

Next, the physical feature information calculator 13a second-order integrates the triaxial acceleration information acquired in the step S7 with respect to a time required until the posture is changed from the first posture to the third posture, and calculates a displacement amount (second displacement information ΔH2) of the wrist of the person to be measured in the process of movement from the first posture to the third posture (step S8).

Next, the physical feature information calculator 13a calculates an upper limb length of the person to be measured by arithmetic processing of the expression (2) based on the second displacement information ΔH2 and a second ratio between the first acceleration information acquired in the step S1 and the third acceleration information acquired in the step S6 (step S9).

Next, the physical feature information calculator 13a subtracts the forearm length calculated in the step S5 from the upper limb length calculated in the step S9 to calculate an upper arm length of the person to be measured, and records the calculated upper arm length into the recording medium 14 (step S10).

By the aforementioned processing, the forearm length and the upper arm length of the person to be measured are recorded in the recording medium 14. In subsequent measurements of blood pressure, the forearm length and the upper arm length are used. A difference in height between the wrist and the heart is calculated in real time by the wrist-heart height difference calculator 13b, and a blood pressure value is corrected by the blood pressure calculator 13c.

According to the blood pressure measuring apparatus 1 as described above, the person to be measured is requested to merely perform the move of moving the arm from the first posture to the second posture and the move of moving the arm from the first posture to the third posture. In this manner, the forearm length and the upper arm length of the person to be measured can be calculated accurately.

Therefore, measurement errors or input mistakes of the forearm length and the upper arm length can be eliminated and blood pressure can be measured accurately, in comparison with a case where the person to be measured measures the forearm length or the upper arm length by himself/herself using a tape measure etc. and manually inputs the measured forearm length or upper arm length. In addition, a burden on the person to be measured can be lightened.

In addition, according to the blood pressure measuring apparatus 1, the person to be measured is requested to assume the postures not to make the angle θ1 in FIG. 3 and the angle θ2 in FIG. 4 equal to 90° but to merely make the angle θ1 in FIG. 3 and the angle θ2 in FIG. 4 larger than 90°.

Thus, the forearm length and the upper arm length can be calculated. Therefore, the person to be measured does not have to be requested to perform difficult moves so that a burden on the person to be measured can be lightened.

In the example of FIG. 4, the arm is raised in a horizontal direction to the front surface of the body so that the arm is moved from the first posture to the third posture. However, the arm may be raised in a vertical direction to the front surface of the body so that the arm is moved from the first posture to the third posture.

Figure 6:
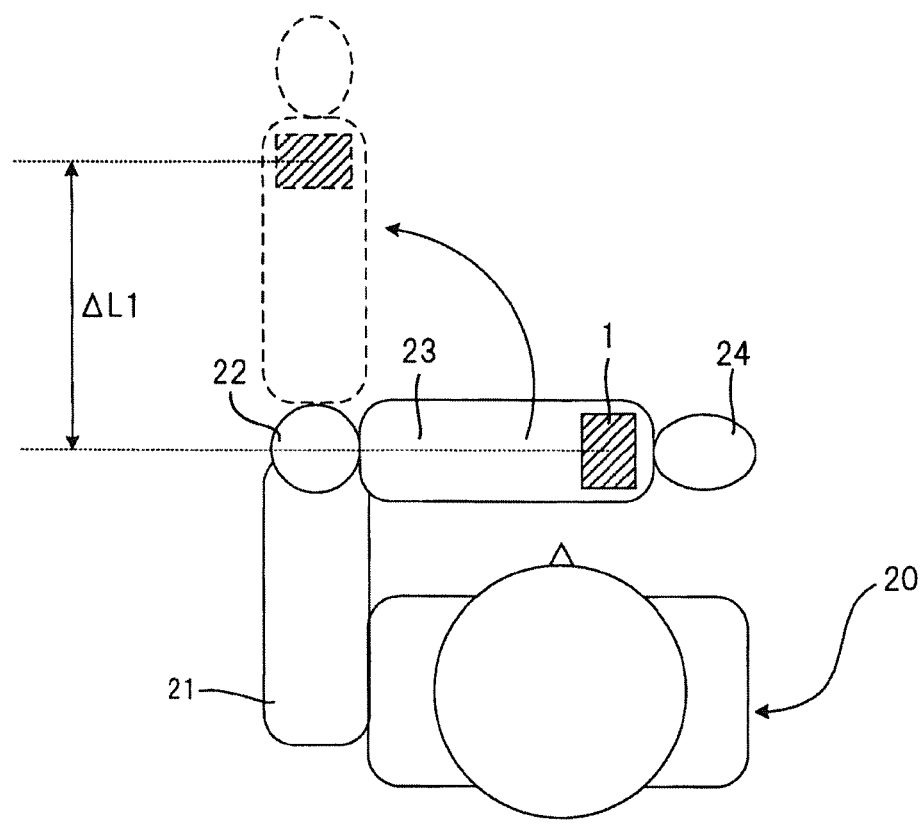
FIG. 6 is a view for explaining a first modification of the forearm length calculating process to be performed by the physical feature information calculator 13a in FIG. 2.

FIG. 6 is a view for explaining a first modification of the forearm length calculating process to be performed by the physical feature information calculator 13a in FIG. 2. FIG. 6 is a top view of a person to be measured 20. In a similar manner to or the same manner as FIG. 3, a left upper arm 21, a left elbow 22, a left forearm 23, and a left hand 24 of the person to be measured 20 are illustrated in FIG. 6.

In the first modification, a state in which a direction connecting a shoulder and the elbow of the person to be measured to each other and a direction connecting the elbow and a wrist of the person to be measured to each other are intersected substantially perpendicularly to each other is regarded as first posture, and a state in which the direction connecting the shoulder and the elbow of the person to be measured to each other and the direction connecting the elbow and the wrist of the person to be measured to each other substantially agree with each other is regarded as second posture.

The physical feature information calculator 13a performs second-order integration in which triaxial acceleration information of a world coordinate system detected by the acceleration sensor 11 in a period of movement from the state of the first posture to the state of the second posture is integrated twice with respect to a time corresponding to the period. Thus, the physical feature information calculator 13a calculates third displacement information ΔL1 [cm], which is a movement amount (a movement amount in a front surface direction of a body of the person to be measured) of the wrist of the person to be measured 20 in the period. The ΔL1 is consistent with a forearm length of the person to be measured.

In the aforementioned manner, the physical feature information calculator 13a can request the person to be measured to assume the first posture and the second posture between which the positions of the shoulder and the elbow are the same but the direction connecting the elbow and the wrist to each other is different (two postures between which the position of the wrist is different), and calculate the forearm length based on acceleration information detected by the acceleration sensor 11 in a process of movement from the first posture to the second posture (or a process of movement from the second posture to the first posture).

In addition, the physical feature information calculator 13a can request the person to be measured to assume the first posture and a third posture between which the position of the shoulder is the same but a direction connecting the shoulder and the wrist to each other is different (two postures between which the position of the wrist is different), and calculate an upper arm length based on acceleration information detected by the acceleration sensor 11 in a process of movement from the first posture to the third posture (or a process of movement from the third posture to the first posture).

The example in which the forearm length, the upper limb length and the upper arm length are calculated as the physical feature information has been described so far. In addition to the forearm length, the upper limb length and the upper arm length, the blood pressure measuring apparatus 1 may also calculate a chest width of the person to be measured as the physical feature information.

Figure 7A:
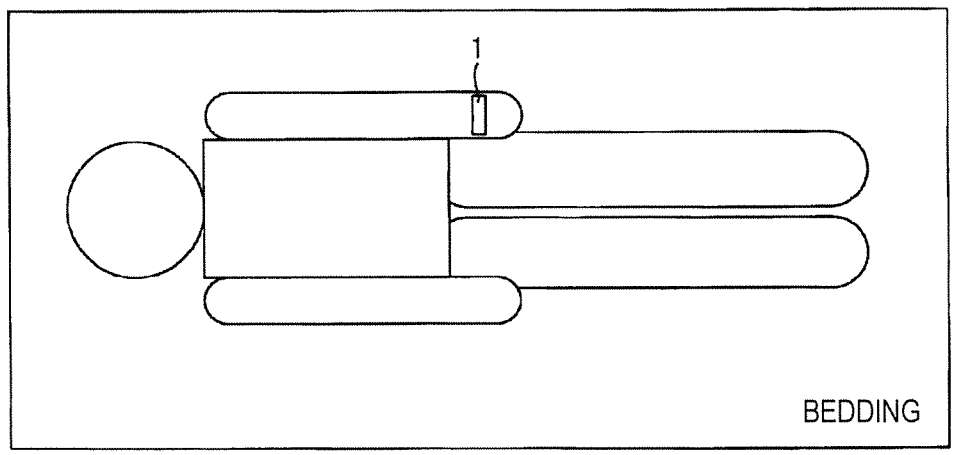
FIGS. 7A, 7B and 7C are views for explaining a calculating process of a chest width of a person to be measured which is performed by the physical feature information calculator 13a in FIG. 2.
Figure 7B:
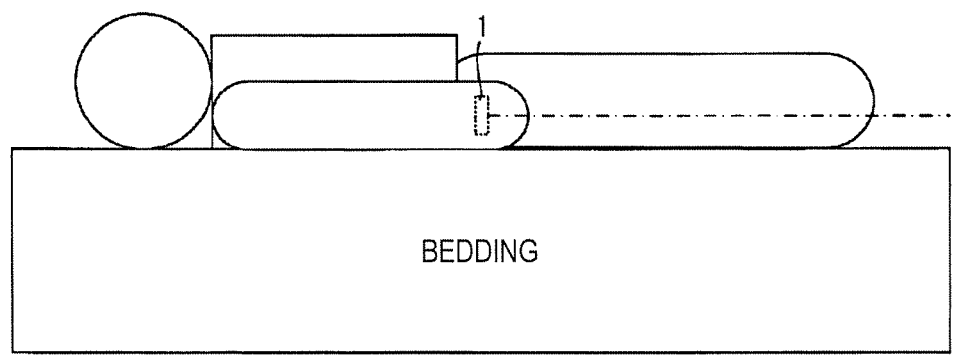
Figure 7C:
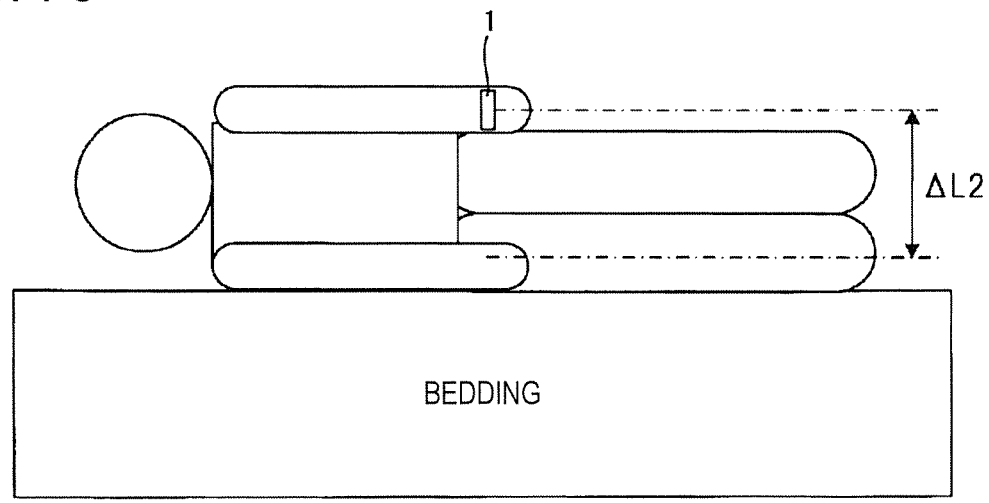

FIGS. 7A to 7C are views for explaining a calculating process of the chest width of the person to be measured which is performed by the physical feature information calculator 13a in FIG. 2.

FIG. 7A shows a state in which the person to be measured who is lying on his/her back (in a supine position) on bedding (a bed or a mattress) places his/her wrist on the bedding. The bedding is provided for people to lie down on. FIG. 7B is a view of FIG. 7A seen from a side of the bedding.

FIG. 7C shows a state in which the person to be measured wearing the blood pressure measuring apparatus 1 on his/her left arm and lying sideways on the bedding with one side of his/her body in contact with the bedding places the left arm on the other side of the body opposite to a contact surface between the body and the bedding.

In the chest width calculating process, a posture of the arm of the person to be measured in the state shown in FIG. 7A and FIG. 7B is regarded as first posture, and a posture of the arm of the person to be measured in the state shown in FIG. 7C is regarded as second posture.

The physical feature information calculator 13a performs second-order integration in which triaxial acceleration information of a world coordinate system detected by the acceleration sensor 11 in a period of movement from the state of the first posture to the state of the second posture (or a period of movement from the second posture to the first posture) is integrated twice with respect to a time corresponding to the period. Thus, the physical feature information calculator 13a calculates fourth displacement information ΔL2 [cm], which is a displacement amount (a displacement of a height in the gravity direction) of the wrist of the person to be measured 20 in the period. The ΔL2 can be handled as a value equal to the chest width of the person to be measured. Therefore, the physical feature information calculator 13a outputs the ΔL2 as the chest width information which is physical feature information.

Incidentally, in the modification, the posture of the arm of the person to be measured who is lying on his/her face (in a prone position) on the bedding and whose wrist is placed on the bedding may be regarded as first posture.

It is possible to empirically determine in advance which part of the chest width of the person the heart is positioned at. Therefore, when the chest width of the person to be measured is known, a gravity-direction distance between the wrist of the person to be measured wearing the blood pressure measuring apparatus 1 in the state of FIG. 7C and the position of the heart of the person to be measured can be estimated.

That is, the wrist-heart height difference calculator 13b can estimate a difference in height between the heart and the blood pressure measuring apparatus 1 based on the chest width information. Accordingly, even when the person to be measured is lying, the blood pressure calculator 13c can calculate a blood pressure value based on the difference in height between the wrist and the heart estimated from the chest width. In this manner, blood pressure can be measured accurately.

According to the physical feature information calculator 13a according to the modification, as described above, the person to be measured is requested to assume the first posture and the second posture between which the position of the wrist is different so that the chest width of the person to be measured can be calculated based on the acceleration information detected by the acceleration sensor 11 in the process of movement from the first posture to the second posture (or in the process of movement from the second posture to the first posture).

The aforementioned program executed by the processor of the controller 13 is provided to be recorded into any of computer-readable non-transitory recording media from which the program can be read by a computer.

For example, such "computer-readable recording media" include an optical medium such as a CD-ROM (Compact Disc-ROM), a magnetic recording medium such as a memory card, etc. In addition, such a program may be also provided by downloading through a network.

It should be conceived that all the points in the embodiment disclosed this time are not limited but merely exemplified. The scope of the invention is defined not by the aforementioned description but by the scope of Claims. All changes having equivalent meaning to the scope of Claims or within the scope of Claims are intended to be included in the scope of the invention.

For example, the blood pressure measuring apparatus 1 is designed to measure the blood pressure value based on the pulse wave detected by the pulse wave detector 10. However, the blood pressure measuring apparatus 1 may be designed to use a cuff to measure the blood pressure value by an oscillometric method, a Korotkoff method, or the like.

As described above, the following items are disclosed in the description of the invention.

The disclosed blood pressure measuring apparatus is a blood pressure measuring apparatus which is adapted to be worn on a wrist of a person to be measured to measure a blood pressure value of the person to be measured, the blood pressure measuring apparatus including: a triaxial acceleration sensor; an information output section which is configured to output information for guiding an arm of the person to be measured on which the blood pressure measuring apparatus is worn, to a pair of a first posture and a second posture between which a position of the wrist is different; a posture determiner which is configured to determine that the arm has been in each of the pair of the postures, based on an output signal of the triaxial acceleration sensor after the output of the information; and a physical feature information calculator which is configured to calculate physical feature information of the person to be measured based on moving acceleration information detected by the triaxial acceleration sensor in a period between when the arm is in one of the pair of the postures and when the arm is in the other of the pair of the postures.

Provided is the disclosed blood pressure measuring apparatus, wherein the first posture and the second posture are postures between which positions of a shoulder and an elbow of the person to be measured are the same but a direction connecting the elbow and the wrist to each other is different, and the physical feature information calculator is configured to calculate a distance between the elbow and the wrist of the person to be measured based on the moving acceleration information.

Provided is the disclosed blood pressure measuring apparatus, wherein the first posture is a posture in which the shoulder, the elbow and the wrist of the person to be measured are arranged in a gravity direction, the second posture is a posture in which the shoulder and the elbow of the person to be measured are arranged in the gravity direction, and an angle between the direction connecting the elbow and the wrist of the person to be measured to each other and the gravity direction is larger than 90°, and the physical feature information calculator is configured to calculate the distance based on first acceleration information detected by the triaxial acceleration sensor when the arm is in the first posture, second acceleration information detected by the triaxial acceleration sensor when the arm is in the second posture, and the moving acceleration information.

Provided is the disclosed blood pressure measuring apparatus, wherein the first posture and the second posture are postures between which a position of a shoulder of the person to be measured is the same but a direction connecting the shoulder and the wrist to each other is different, and the physical feature information calculator is configured to calculate a distance between the shoulder and the wrist of the person to be measured based on the moving acceleration information.

Provided is the disclosed blood pressure measuring apparatus, wherein the first posture is a posture in which the shoulder, an elbow and the wrist of the person to be measured are arranged in a gravity direction, the second posture is a posture in which an angle between a direction connecting the shoulder, the elbow and the wrist of the person to be measured to one another and the gravity direction is larger than 90°, and the physical feature information calculator is configured to calculate the distance based on first acceleration information detected by the triaxial acceleration sensor when the arm is in the first posture, second acceleration information detected by the triaxial acceleration sensor when the arm is in the second posture, and the moving acceleration information.

Provided is the disclosed blood pressure measuring apparatus, wherein the physical feature information calculator is configured to calculate displacement information of the wrist of the person to be measured in the gravity direction based on the moving acceleration information, and calculates the distance based on the displacement information and a ratio of an absolute value of the first acceleration information to a sum of the absolute value of the first acceleration information and an absolute value of the second acceleration information.

Provided is the disclosed blood pressure measuring apparatus, wherein the physical feature information calculator is configured to multiply the displacement information by the ratio to calculate the distance.

Provided is the disclosed blood pressure measuring apparatus, wherein the first posture is a posture in which the person to be measured who is lying on bedding places the wrist of the person to be measured on the bedding, the bedding being provided for the person to be measured to lie down on, the second posture is a posture in which the person to be measured who is lying sideways on the bedding with one side of a body of the person to be measured in contact with the bedding places the wrist on the other side of the body opposite to a contact surface between the person to be measured and the bedding, and the physical feature information calculator is configured to calculate displacement information of the wrist of the person to be measured in a gravity direction based on the moving acceleration information, and is configured to output the displacement information as chest width information of the person to be measured.

Provided is the disclosed blood pressure measuring apparatus, further including: a blood pressure calculator which is configured to calculate a blood pressure value based on the physical feature information calculated by the physical feature information calculator.

The disclosed physical feature information calculating method is a physical feature information calculating method for calculating physical feature information of a person, the physical feature information calculating method including: an information outputting step of outputting information for guiding an arm of the person to a pair of a first posture and a second posture between which a position of a wrist of the person is different; a posture determining step of determining that the arm has been in each of the pair of the postures based on an output signal of a triaxial acceleration sensor after the output of the information, the triaxial acceleration sensor adapted to be worn on the wrist of the person; and a physical feature information calculating step of calculating the physical feature information of the person based on moving acceleration information detected by the triaxial acceleration sensor in a period between when the arm is in one of the pair of the postures and when the arm is in the other of the pair of the postures.

The disclosed physical feature information calculating program is a program which causes a computer to execute the respective steps of the aforementioned physical feature information calculating method.

The invention is particularly applied to a wrist type blood pressure measuring apparatus so as to be high in user-friendliness and effective.

According to the invention, it is possible to provide a blood pressure measuring apparatus, a physical feature information calculating method and a physical feature information calculating program, in which body part feature information of a person to be measured necessary for calculating a difference in height between a measured part and a heart can be obtained accurately by simple work.

Although the invention has been described based on a specific embodiment, the invention is not limited to the embodiment. Various changes can be however made on the invention without departing from the technical concept of the disclosed invention.

What is claimed is:

1. A blood pressure measuring apparatus which is adapted to be worn on a wrist of a person to be measured to measure a blood pressure value of the person to be measured, the blood pressure measuring apparatus comprising:
   a triaxial acceleration sensor; and
   a controller, wherein the controller is configured:
   to output information for guiding an arm of the person to be measured on which the blood pressure measuring apparatus is worn, to a first posture and a second posture where a position of the wrist differs in the first posture and the second posture;
   to determine that the arm has been in both the first posture and the second posture, based on an output signal of the triaxial acceleration sensor after the output of the information; and
   to calculate physical feature information associated with an upper limb of the person to be measured based on moving acceleration information detected by the triaxial acceleration sensor in a period between when the arm is in a one posture of the first posture and the second posture and when the arm is in an other posture of the first posture and the second posture,
   wherein, in the first posture and the second posture, a position of a shoulder and a position of an elbow of the person to be measured are unchanged but a direction connecting the elbow and the wrist to each other is different, and
   wherein the controller is further configured to calculate a distance between the elbow and the wrist of the person to be measured based on the moving acceleration information,
   wherein, in the first posture, the shoulder, the elbow, and the wrist of the person to be measured are linearly arranged parallel to a gravity direction, wherein, in the second posture, the shoulder and the elbow of the person to be measured are linearly arranged parallel to the gravity direction, and an angle between the direction connecting the elbow and the wrist of the person to be measured to each other and the gravity direction is larger than 90°, and wherein calculating the distance between the elbow and the wrist also uses first acceleration information detected by the triaxial acceleration sensor when the arm is in the first posture and second acceleration information detected by the triaxial acceleration sensor when the arm is in the second posture.

2. The blood pressure measuring apparatus according to claim 1, wherein the controller is further configured to calculate displacement information of the wrist of the person to be measured in the gravity direction based on the moving acceleration information, and is further configured to calculate the distance also using the displacement information and a ratio of an absolute value of the first acceleration information to a sum of the absolute value of the first acceleration information and an absolute value of the second acceleration information.

3. The blood pressure measuring apparatus according to claim 2, wherein the controller is further configured to multiply the displacement information by the ratio to calculate the distance.

4. The blood pressure measuring apparatus according to claim 1, wherein the controller is further configured to calculate a blood pressure value based on the physical feature information.

5. A physical feature information calculating method for calculating physical feature information of a person, the physical feature information calculating method comprising:

outputting information for guiding an arm of the person to a first posture and a second posture where a position of a wrist of the person differs in the first posture and the second posture;

determining that the arm has been in both the first posture and the second posture based on an output signal of a triaxial acceleration sensor after the output of the information, the triaxial acceleration sensor adapted to be worn on the wrist of the person; and calculating the physical feature information associated with an upper limb of the person based on moving acceleration information detected by the triaxial acceleration sensor in a period between when the arm is in a one posture of the first posture and the second posture and when the arm is in an other posture of the first posture and the second posture, wherein, in the first posture and the second posture, a position of a shoulder and a position of an elbow of the person to be measured are unchanged but a direction connecting the elbow and the wrist to each other is different, and wherein the method further includes calculating a distance between the elbow and the wrist of the person to be measured based on the moving acceleration information, wherein, in the first posture, the shoulder, the elbow, and the wrist of the person to be measured are linearly arranged parallel to a gravity direction, wherein, in the second posture, the shoulder and the elbow of the person to be measured are linearly arranged parallel to the gravity direction, and an angle between the direction connecting the elbow and the wrist of the person to be measured to each other and the gravity direction is larger than 90°, and wherein calculating the distance between the elbow and the wrist also uses first acceleration information detected by the triaxial acceleration sensor when the arm is in the first posture and second acceleration information detected by the triaxial acceleration sensor when the arm is in the second posture.

6. A non-transitory computer readable medium in which a program causing a computer to execute the method according to claim 5 is recorded.

7. A blood pressure measuring apparatus which is adapted to be worn on a wrist of a person to be measured to measure a blood pressure value of the person to be measured, the blood pressure measuring apparatus comprising:

a triaxial acceleration sensor; and
a controller, wherein the controller is configured:

to output information for guiding an arm of the person to be measured on which the blood pressure measuring apparatus is worn, to a first posture and a second posture where a position of the wrist differs in the first posture and the second posture;

to determine that the arm has been in both the first posture and the second posture, based on an output signal of the triaxial acceleration sensor after the output of the information; and to calculate physical feature information associated with an upper limb or of the person to be measured based on moving acceleration information detected by the triaxial acceleration sensor in a period between when the arm is in a one posture of the first posture and the second posture and when the arm is in another posture of the first posture and the second posture, wherein, in the first posture and the second posture, a position of a shoulder of the person to be measured is unchanged but a direction connecting the shoulder and the wrist to each other is different, and wherein the controller is further configured to calculate a distance between the shoulder and the wrist of the person to be measured based on the moving acceleration information, wherein, in the first posture, the shoulder, an elbow, and the wrist of the person to be measured are linearly arranged parallel to a gravity direction, wherein, in the second posture, an angle between a direction connecting the shoulder, the elbow, and the wrist of the person to be measured to one another and the gravity direction is larger than 90°, and wherein calculating the distance between the shoulder and the wrist also uses first acceleration information detected by the triaxial acceleration sensor when the arm is in the first posture and second acceleration information detected by the triaxial acceleration sensor when the arm is in the second posture.

8. The blood pressure measuring apparatus according to claim 7, wherein the controller is further configured to calculate displacement information of the wrist of the person to be measured in the gravity direction based on the moving acceleration information, and is further configured to calculate the distance also using the displacement information and a ratio of an absolute value of the first acceleration information to a sum of the absolute value of the first acceleration information and an absolute value of the second acceleration information.

9. The blood pressure measuring apparatus according to claim 8, wherein the controller is further configured to multiply the displacement information by the ratio to calculate the distance.

10. The blood pressure measuring apparatus according to claim 7, wherein the controller is further configured to calculate a blood pressure value based on the physical feature information.

11. A physical feature information calculating method for calculating physical feature information of a person, the physical feature information calculating method comprising:
    outputting information for guiding an arm of the person to a first posture and a second posture where a position of a wrist of the person differs in the first posture and the second posture;
    determining that the arm has been in both the first posture and the second posture based on an output signal of a triaxial acceleration sensor after the output of the information, the triaxial acceleration sensor adapted to be worn on the wrist of the person; and
    calculating the physical feature information associated with an upper limb of the person based on moving acceleration information detected by the triaxial acceleration sensor in a period between when the arm is in a one posture of the first posture and the second posture and when the arm is in an other posture of the first posture and the second posture,
    wherein, in the first posture and the second posture, a position of a shoulder of the person to be measured is unchanged but a direction connecting the shoulder and the wrist to each other is different, and
    wherein the method further includes calculating a distance between the shoulder and the wrist of the person to be measured based on the moving acceleration information,
    wherein, in the first posture, the shoulder, an elbow, and the wrist of the person to be measured are linearly arranged parallel to a gravity direction,
    wherein, in the second posture, an angle between a direction connecting the shoulder, the elbow, and the wrist of the person to be measured to one another and the gravity direction is larger than 90°, and
    wherein calculating the distance between the shoulder and the wrist also uses first acceleration information detected by the triaxial acceleration sensor when the arm is in the first posture and second acceleration information detected by the triaxial acceleration sensor when the arm is in the second posture.

12. A non-transitory computer readable medium in which a program causing a computer to execute the method according to claim 11 is recorded.

* * * * *